United States Patent [19]

Gatlin et al.

[11] Patent Number: 4,567,274

[45] Date of Patent: Jan. 28, 1986

[54] CHLORINE EXCHANGE FOR FLUORINE IN 2-FLUOROPYRIDINE COMPOUNDS

[75] Inventors: Janice E. Gatlin, Antioch; Mark A. Van Dort, Pleasant Hill; Charles A. Wilson, Pittsburg; Alexander P. Fung, Martinez, all of Calif.

[73] Assignee: The Dow Chemical Company, Midland, Mich.

[21] Appl. No.: 675,036

[22] Filed: Nov. 26, 1984

[51] Int. Cl.[4] .......................................... C07D 211/72
[52] U.S. Cl. .................................................. 546/345
[58] Field of Search ........................................ 546/345

[56] References Cited

U.S. PATENT DOCUMENTS 4,393,214  7/1983  Roberts et al. ...................... 546/345

Primary Examiner—Henry R. Jiles
Assistant Examiner—Robert C. Whittenbaugh
Attorney, Agent, or Firm—Merlin B. Davey

[57] ABSTRACT

A method of exchanging a chlorine atom for a fluorine atom at the 2-position of a 2-fluoropyridine compound which comprises contacting a 2-fluoropyridine compound with a substituted or unsubstituted trichloromethyl or dichlorofluoromethyl alpha, beta or gamma picoline compound at a temperature of 50°–250° C. and a pressure of atmospheric to about 100 psig.

10 Claims, No Drawings

CHLORINE EXCHANGE FOR FLUORINE IN 2-FLUOROPYRIDINE COMPOUNDS

BACKGROUND OF THE INVENTION

The present invention relates to a method of exchanging chlorine atoms for fluorine atoms in 2-fluoro-pyridine compounds.

2-chloropyridine compounds, for example, 2-chloro-5-(trifluoromethyl)pyridine, are commercially valuable chemical intermediates useful in the preparation of medicinal agents and agricultural chemicals. The 2-chloro-5-(trifluoromethyl)pyridine compounds are generally prepared by fluorinating a (trichloromethyl)pyridine compound.

Problems associated with the preparation of, e.g., 2-chloro-5-(trifluoromethyl)pyridine and other such compounds include (1) an over fluorinated end product, i.e., 2-fluoro-5-(trifluoromethyl)pyridines, and (2) the formation of a 2-fluoro isomer of the desired (trifluoromethyl)pyridine product generally described as a 2-fluoro-5(chlorodifluoromethyl)pyridine compound. These 2-fluoro-pyridine by-products reduce the yield of the desired (trifluoromethyl)pyridines and necessitate additional separatory procedures which are both bothersome and expensive. The 2-fluoro isomer is a particularly annoying by-product because of the difficulty in separating it from the desired (trifluoromethyl)pyridine product.

EPO Application No. 80201077.7 (Publication No.: 0 028,870) teaches the preparation of 2-chloro-5-(trifluoromethyl)pyridine compounds employed as intermediates in the preparation of 2-pyridinyloxy(or thio)-phenoxy alkanoic acids and derivatives thereof which are herbicides. It discloses that the formation of the 2-fluoro pyridine is of no practical disadvantage since the halogen at the 2-position is displaced in the subsequent reaction with the metal salt of the hydroxy phenoxy alkanoic acid compound. Having fluorine in the 2-pyridine ring position poses a waste stream problem with a metal fluoride (KF, NaF) when compared to a waste stream of NaCl or KCl when chlorine is in the 2-pyridine ring position. Furthermore, converting the 2-fluoro pyridine compounds to 2-chloro pyridine compounds according to the present invention allows for the recovery of HF which can be recycled for use as a fluorinating agent. It is clearly evident that there is a need for a method of converting the 2-fluoro-pyridine by-products to the desired 2-chloro-pyridine compounds. U.S. patent application Ser. No. 417,724, filed Sept. 13, 1982, teaches a method of exchanging a chlorine atom for a fluorine atom at the 2-position of a a 2-fluoropyridine compound which comprises contacting said compound with HCl in the absence of a catalyst at a superatmospheric pressure and at a temperature from about 50° C. to about 200° C.

SUMMARY OF THE INVENTION

It has now been found possible to replace the fluorine atom in the 2-position of the pyridine ring of a 2-fluoropyridine compound with a chlorine atom by contacting said 2-fluoropyridine compound with a substituted or unsubstituted trichloromethyl or dichlorofluoromethyl alpha, beta or gamma picoline compound at a temperature of 50°–250° C. and a pressure of atmospheric to 100 psig. The chlorinated products of this method are useful as intermediates in the synthesis of biologically active compounds, such as medicinals and herbicides.

Of particular interest in the practice of this invention is a method of replacing the fluorine atom at the 2-ring position of 3-chloro-2-fluoro-5-(trifluoromethyl)pyridine with a chlorine atom yielding 2,3-dichloro-5-(trifluoromethyl)pyridine, an intermediate in the manufacture of agricultural chemicals.

Also of interest are methods of replacing the fluorine atoms at the 2-position of 2-fluoro-5-(trifluoromethyl)-pyridine; 3-chloro-2-fluoro-5-(chlorodifluoromethyl)-pyridine; and 2-fluoro-5-(chlorodifluoromethyl)pyridine with a chlorine atom yielding 2-chloro-5-(trifluoromethyl)- or (chlorodifluoromethyl)pyridine compounds with or without chlorine in the 3-position.

DETAILED DESCRIPTION OF THE EMBODIMENTS

In conducting the present reaction, a 2-fluoropyridine compound is contacted with a substituted or unsubstituted trichloromethyl or dichloromethyl alpha, beta or gamma picoline compound at a pressure of atmospheric to 100 psig and advantageously at a temperature in the range of from about 50° C. to about 250° C.

2-Fluoro-pyridine compounds include 3-chloro-2-fluoro-5-(trifluoromethyl)pyridine, 2-fluoro-5-(trifluoromethyl)pyridine, 2,3-difluoro-5-(trifluoromethyl)pyridine, and the above compounds wherein -chlorodifluoromethyl or -dichlorofluoromethyl groups are substituted for the trifluoromethyl groups. The 2-fluoro-pyridine compounds can be reacted separately or as a mixture containing more than one 2-fluoro-pyridine compound.

In a preferred embodiment, a mixture containing chlorinated-(trichloromethyl)pyridines and one or more 2-fluoro-pyridine compounds is reacted according to the present invention whereby a chlorine atom is exchanged for the fluorine atom attached to the 2-position of the pyridine ring. The above mixtures are advantageously obtained from the reaction products in the preparation of (trifluoromethyl)pyridine compounds such as, for example, 2,3-dichloro-5-(trifluoromethyl)-pyridine and 2-chloro-5-(trifluoromethyl)pyridine, whereby the 2-fluoro-pyridine compounds are undesirable by-products.

The employment of a chloropyridine as the chlorinating agent is a critical component of the present invention and HCl may or may not be employed as desired. Suitable chlorinating agents are preferably supplied in amounts to provide at least about one mole of chlorine atoms per mole of fluorine atoms to be displaced on the 2-fluoro-pyridine compounds. An excess of chlorinating agent is preferably employed and is not detrimental to the present process.

Generally, the present reaction is conducted neat or in the absence of a solvent.

In practicing the present invention, pressures from atmospheric to superatmospheric pressures may be employed. The present reaction is advantageously conducted at a pressure of at least about 5 psig and usually at a pressure of from about 25 to about 100 psig, while 40–50 psig represents a preferred pressure. The upper pressure, i.e., 100 psig, is not meant to be a limitation of the present invention but is only set forth as an economical consideration. Conducting the present reaction at a superatmospheric pressure provides conversion of the 2-fluoro-pyridines to their corresponding 2-chloro analogs at an accelerated rate when compared to conducting the reaction at atmospheric pressure. Furthermore, the reaction can be run in the absence of a catalyst and excellent yields of the desired products (about 98 percent of theoretical) can be obtained.

The present reaction is advantageously conducted in the liquid phase at a temperature of between about 50° C. and about 250° C. and preferably between about 140° C. and about 190° C. A particularly preferred temperature to conduct the present reaction is about 185° C. The present reaction is typically conducted in the presence of agitation sufficient to disperse the chlorinating agent in the liquid phase.

In conducting the present reaction, neither the rate of addition of the chlorinating agent nor the order of addition of the reactants is critical. Preferably, the suitable chlorinating agent is added in liquid form to the 2-fluoro-pyridine compounds. A typical reaction according to the present invention generally requires from about ½ to about 24 hours to be substantially complete.

The present reaction can be characterized as follows:

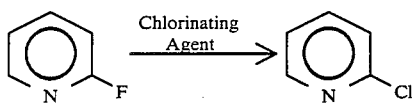

The pyridine ring may optionally contain other substituents in the other ring positions, such as —F, —Cl, —CCl$_3$, —CF$_3$, —CClF$_2$ and —CCl$_2$F. Of particular interest are reactions involving 2-fluoro-pyridine compounds which are characterized as follows:

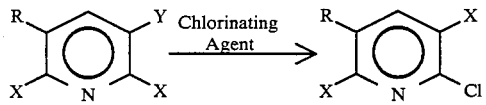

wherein
R represents —H, —CF$_3$, —CF$_2$Cl, —CCl$_2$F, or CCl$_3$; each X independently represents F, Cl or H with the proviso that at least one X is always F; and Y represents F, Cl or H. No attempt has been made to balance the above equations.

In a preferred embodiment of the present invention, the reaction product in the preparation of 2-chloro-5-(trifluoromethyl)pyridine, which contains 2-fluoro-pyridines, such as, 2-fluoro-5-(trifluoromethyl)pyridine and 2-fluoro-5-(chlorodifluoromethyl)pyridine, in addition to the desired 2-chloro-5-(trifluoromethyl)pyridine, is contacted with 2-chloro-5-trichloromethylpyridine in the presence of FeCl$_3$ at elevated temperatures as described herein to convert the 2-fluoro-pyridines to their corresponding 2-chloro analogs. The desired 2-chloro-5-(trifluoromethyl)pyridine is then readily separable from the reaction mixture by distillation since the 2-fluoro isomer, i.e. 2-fluoro-5-(chlorodifluoromethyl)-pyridine, is converted to 2-chloro-5-(chlorodifluoromethyl)pyridine which has a boiling point different from the desired product.

In an especially preferred embodiment of the present invention, the reaction product in the preparation of 2,3-dichloro-5-(trifluoromethyl)pyridine, which contains 2-fluoro-pyridines, such as, 3-chloro-2-fluoro-5-(trifluoromethyl)pyridine and 3-chloro-2-fluoro-5-(chlorodifluoromethyl)pyridine, in addition to the desired 2,3-dichloro-5-(trifluoromethyl)pyridine, is contacted with 2,3-dichloro-5-trichloromethylpyridine in the presence of FeCl$_3$ at elevated temperatures as described herein to convert the 2-fluoro-pyridines to their corresponding 2-chloro analogs. The desired 2,3-dichloro-5-(trifluoromethyl)pyridine is then readily separable from the reaction mixture by distillation since the 2-fluoro isomer, i.e., 3-chloro-2-fluoro-5-(chlorodifluoromethyl)pyridine, is converted to 2,3-dichloro-5-(chlorodifluoromethyl)pyridine which has a boiling point different from the desired product.

In a further preferred embodiment, 2-chloro-3-fluoro-5-(trifluoromethyl)pyridine is prepared by the reaction of 2,3-dichloro-5-(trichloromethyl)pyridine and 2,3-difluoro-5-(trifluoromethyl)pyridine in the presence of FeCl$_3$ catalyst at superatmospheric pressure in the absence of any added HCl.

This invention is further illustrated by the following Examples.

EXAMPLE 1

1200 grams of 2,3-penta(2,3-dichloro-5-(trichloromethylpyridine) (97.1% pure) and 5 mole % FeCl$_3$ were added to a one liter, hastelloy C Parr reactor fitted with heater, magnetic stirrer, condensers (kept at about 17°–20° C.), pressure control, HF feed system and 2,3-penta feed system. The material was heated to 176° C. under 40 psig nitrogen. Once the 176° C. setpoint was reached, HF feed was begun. 15.1 g/hr HF was fed for 10 hours. The rate was then reduced to 10.2 g/hr for the next 17 hours. It was then further reduced to 3.2 g/hr for the final 10.75 hours. At 37.75 hours (there was 29% ring tetra,

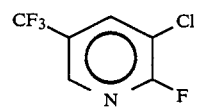

2.6% ring tri,

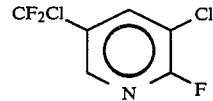

and 57.2% trifluoro product)

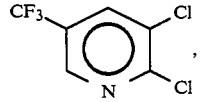

the HF was shut off and 161.4 grams 2,3-penta was added. The temperature and pressure were kept at 175° C. and 41 psig respectively. The reaction with 2,3-penta was allowed to continue for 3 hours. After these 3 hours, an additional 80.7 grams 2,3-penta was added and the reaction allowed to continue an additional 7.5 hours. At the end of this time, only 1.8% ring tetra remained, 0.4% ring tri was left and the trifluoro product had increased to 68.9%.

EXAMPLE 2

2.1 moles (584 g) of 2,3-penta (97%) and 2.0 moles (483 g) of ring tetra (99%) and 4.6 mole % FeF$_3$ were placed in above reactor system. A sample of this mixture, taken before any reaction occured, showed 35.5% ring tetra, 8% tri product, and 50.3% 2,3-penta. The material was heated under 40.8 psig nitrogen. Once the setpoint of 175° C. was reached, the analysis showed that ⅔ of the ring tetra had already reacted away and 28.5% product had been made. The reaction was allowed to continue for 4.75 hours. At this time, only 1.9% ring tetra and 11% 2,3-penta remained; about 24% monofluoro and about 10% difluoro (product precursors) had been made and there was about 47% trifluoro product.

EXAMPLE 3

584 g 2,3-penta (97%) and 400 g ring tetra (99%) were placed in above mentioned reactor system, heated at 175° C., under 40.6 psig nitrogen for 8 hours. (This starting mixture contained 0.04% and 0.09% F$^-$ and Cl$^-$, respectively). At the end of the 8 hours, the ring tetra had been reduced from about 40% to 33%, the 2,3-penta from about 58% to about 46%, and about 9% mono and 10% tri product had been made.

EXAMPLE 4

1200 g 2,3-penta (98.9%) and 5 mole % FeCl$_3$ was added to reactor, heated to about 175° C. at 40 psig. 17.2 g/hr HF feed was begun once the mixture reached the temperature setpoint and continued for 10 hours. The HF feed rate was then reduced to 9.8 g/hr for the next 21 hours.

At the end of this forward reaction, 128.5 g 2,3-penta was added (no HCl was added) at 140° C. and about 6 psig and let react for 2 hours. Ring tetra was reduced from 20% to 13%, ring tri was reduced from about 4% to about 1%; product increased from about 45% to 61%.

EXAMPLE 5

1200 g 2,3-penta (97.3%) and 5 mole % FeCl$_3$ were heated to 175° C. at 40 psig, and HF was added in three steps with varying feed rates as follows: 16.4 g/hr for 10 hours, 10.7 g/hr for next 15 hours, then 3.5 g/hr for last 7 hours. At the end of this forward reaction, 113 g 2,3-penta was added and the reaction mixture let react at 141° C. and 20 psig for 2 hours. The ring tetra concentration was reduced from 21% to about 10%; ring tri from 4.5% to about 3%; and the tri product was increased from 46% to 61%.

EXAMPLE 6

2.0 Moles (531 g) of 2,3-penta (99%) and 2 moles (366 g) of 2,3-difluoro-5-(trifluoromethyl)pyridine (99%) and 5 weight percent FeCl$_3$ catalyst (47 g) were placed in the reactor system employed in Example 2. This starting mixture contained 56.3 weight percent 2,3-penta and 38.8 weight percent of the pentafluoro compound. The mixture was heated at 120° C. under 70 psig nitrogen for four hours at which time analysis showed the following results.

| Compound | Wt. % |
| --- | --- |
| 2,3-dichloro-5-(trichloromethyl)pyridine | 1.7 |
| 2,3-dichloro-5-(dichlorofluoromethyl)pyridine | 36.2 |
| 2,3-dichloro-5-(chlorodifluoromethyl)pyridine | 14.5 |
| 2,3-difluoro-5-(trifluoromethyl)pyridine | 1.2 |
| 2-chloro-3-fluoro-5-(trifluoromethyl)pyridine | 41.4 |

EXAMPLE 7

A 480 ml Teflon ®-PFA reaction flask, fitted with a PFA reflux condenser, an HF/HCl bleed tube, and a magnetic stirrer, were changed with 8.9 grams of anhydrous FeCl$_3$ and 180 grams of 2-chloro-5-trichloromethylpyridine. Anhydrous HF gas was continuously sparged into the reaction mixture at a rate of about 4 g/hr as the mixture was heated to a temperature of 170° C. and maintained at this temperature for 21 hours. It was then reduced to 150°–160° C. for an additional 10 hours. At 31 hours, there was 27.3% 2-fluoro-5-trifluoromethylpyridine, 6.8% 2-fluoro-5-chlorodifluoromethylpyridine, 51.6% trifluoromethyl product, and 4.3% 2-chloro-5-chlorodifluoromethylpyridine. The HF was shut off and 50 grams of 2-chloro-5-trichloromethylpyridine was added. The temperature was kept at 140° C. and the reaction was allowed to continue for another 8 hours. At the end of this time, only 1.0% of 2-fluoro-5-trifluoromethylpyridine remained, 0.6% of 2-fluoro-5-chlorodifluoromethylpyridine was left and the trifluoromethyl product had increased to 61.0%.

EXAMPLE 8

A mixture containing 100 grams of 2,3-difluoro-5-trifluoromethylpyridine, 50 grams of 2,3-dichloro-5-trichloromethylpyridine and 7.5 grams of FeCl$_3$ was heated to approximately 150° C. at atmospheric pressure for 11 hours with constant agitation. Analysis of the final composition of the mixture showed as follows:

| Compound | Area percent by gas Chromatography |
| --- | --- |
| 2,3-difluoro-5-(trifluoromethyl)pyridine | 37.6 |
| 2-chloro-3-fluoro-(trifluoromethyl)pyridine | 29.3 |
| 2,3-dichloro-(trifluoromethyl)pyridine | 0.9 |
| 2,3-dichloro-5-(chlorodifluoromethyl)pyridine | 13.0 |
| 2,3-dichloro-5-(dichlorofluoromethyl)pyridine | 15.6 |
| 2,3-dichloro-5-(trichloromethyl)pyridine | 4.6 |

What is claimed is:

1. A method of exchanging a chlorine atom for a fluorine atom at the 2-position of a 2-fluoropyridine compound which comprises contacting a 2-fluoropyridine compound with a halosubstituted or unsubstituted trichloromethyl or dichlorofluoromethyl alpha, beta or gamma picoline compound in liquid phase at a temperature of 50°–250° C. and a pressure of atmospheric to about 100 psig.

2. Method of claim 1 wherein the picoline compound employed is 2,3-dichloro-5-(trichloromethyl)pyridine.

3. Method of claim 2 wherein the 2-fluoropyridine compound is 3-chloro-2-fluoro-5-(trifluoromethyl)pyridine, 3-chloro-2-fluoro-5-(chlorodifluoromethyl)pyridine, 2,3-difluoro-5-(trifluoromethyl)pyridine or a mixture thereof.

4. Method of claim 3 wherein the method is carried out in the presence of FeCl$_3$.

5. Method of claim 4 wherein the catalyst is FeCl$_3$.

6. Method of claim 2 wherein the method is carried out in the presence of HCl.

7. Method of claim 2 wherein the method is carried out in the absence of HCl.

8. Method of claim 3 wherein the method is carried out in the presence of FeF$_3$.

9. Method of claim 1 wherein the picoline compound employed is 2-chloro-5-(trichloromethyl)pyridine.

10. Method of claim 9 wherein the 2-fluoro-pyridine compound is 2-fluoro-5-trifluoromethylpyridine, 2-fluoro-5-chlorodifluoromethylpyridine, or a mixture thereof.

* * * * *

UNITED STATES PATENT AND TRADEMARK OFFICE
CERTIFICATE OF CORRECTION

PATENT NO. : 4,567,274

DATED : January 28, 1986

INVENTOR(S) : Janice E. Gatlin, Mark A. Van Dort, Charles A. Wilson, Alexander P. Fung It is certified that error appears in the above-identified patent and that said Letters Patent is hereby corrected as shown below:

Column 1, line 53, "of a a" should read --of a--.

Column 6, delete claim 5 in its entirety.

On the title page "10 Claims, No Drawings" should read --9 Claims, No Drawings--.

Signed and Sealed this

Second Day of December, 1986

Attest:

DONALD J. QUIGG

Attesting Officer

Commissioner of Patents and Trademarks